United States Patent [19]

Lapeyre

[11] 4,278,095

[45] Jul. 14, 1981

[54] EXERCISE MONITOR SYSTEM AND METHOD

[76] Inventor: Pierre A. Lapeyre, P.O. Box 430, Houma, La. 70360

[21] Appl. No.: 45,627

[22] Filed: Jun. 5, 1979

Related U.S. Application Data

[63] Continuation of Ser. No. 831,666, Sep. 12, 1977, abandoned.

[51] Int. Cl.$^3$ ............................................. A61B 5/04
[52] U.S. Cl. .................................. 128/689; 128/707; 272/69
[58] Field of Search .............. 128/696, 706, 707, 709, 128/689; 272/69–73, 99, 97, 100, DIG. 5, DIG. 6; 273/86 B, DIG. 28; 73/379

[56] References Cited

U.S. PATENT DOCUMENTS

| | | | |
|---|---|---|---|
| 3,159,400 | 12/1964 | Brass et al. | 35/29 R |
| 3,419,732 | 12/1968 | Lane | 272/73 UX |
| 3,454,942 | 7/1969 | Chamberlin, Jr. et al. | 272/DIG. 6 |
| 3,518,985 | 7/1970 | Quinton | 128/707 |
| 3,542,012 | 11/1976 | Frieberger et al. | 35/29 R UX |
| 3,675,640 | 7/1972 | Gatts | 272/DIG. 6 X |
| 3,834,702 | 9/1974 | Bliss | 273/86 B |
| 3,845,756 | 11/1974 | Olsson | 272/DIG. 6 X |
| 3,903,613 | 9/1975 | Bisberg | 35/11 R |
| 3,991,307 | 11/1976 | Hillsman | 128/720 X |
| 4,063,551 | 12/1977 | Sweeney | 128/666 |
| 4,112,928 | 9/1978 | Putsch | 128/707 |
| 4,141,630 | 2/1979 | Emmons | 272/73 X |

FOREIGN PATENT DOCUMENTS 966865  4/1975  Canada ....................................... 272/69

Primary Examiner—Robert W. Michell
Assistant Examiner—Francis J. Jaworski
Attorney, Agent, or Firm—Wilkinson, Mawhinney & Theibault

[57] ABSTRACT

The invention encourages optimal exercise, particularly of the aerobic type, for cardiovascular fitness. The user powers an exerciser, such as a treadmill, simulated cycling or rowing, and the like, and a monitor displays the users speed and distance accomplished. A variable speed outdoor exercising scene (such as a person rowing a boat) is shown to the user when the monitor is a TV set. The users speed signal controls the speed of a videotape cassette player to proportionately change the speed of the outdoor exercising scene. The speed signal is converted to the reciprocal of speed i.e., minutes per mile and the distance is displayed to hundredths of miles. The latter two signals are converted to BCD digits and superimposed on the video through a TV positioning and generation circuit for display on the scene. The heart beat is picked up electrically or by infra red and converted into three digits of beats per minute, and also superimposed on the video for display on the monitor. In addition, the users pulse rate or heart beat is displayed.

2 Claims, 7 Drawing Figures

EXERCISE MONITOR SYSTEM AND METHOD

This is a continuation of application Ser. No. 831,666, filed Sept. 12, 1977, now abandoned.

FIELD OF THE INVENTION

It has been found that only aerobic exercises promote cardiovascular fitness. This is because they significantly increase the continuous flow of blood through the heart and large skeletal muscles. The better aerobic exercises are walking briskly, jogging, cycling at rapid speed, running, swimming, ice or roller skating, and rope skipping.

Fitness exercise problems are twofold; first, the exercises which generally move both arms and legs vigorously should be sustained at target level for 20 minutes or longer. The target zone is between 70 and 85 percent of the maximal attainable heart rate, roughly 220 minus the users age in years. Women reach the same maximal heartbeats as men of comparable age. Below 70 percent of the target zone capacity, there is little fitness benefit from exercise for the purposes hereof. Above 85 percent there is little added benefit from extra exercise.

Secondly, the user must presently take his own pulse count at 5 minute intervals to determine the vigor needed for target zone.

Obviously, the display of the heartbeat is of tremendous value for an aerobic exercise program, and the display of the personal parameters and speed controlled scene are motivating.

Such a fitness program consists of three basic stages, mainly warm-up, target zone, and cool down. The warm-up period should consume 5 to 10 minutes and the heartbeat should be less than 50 percent of the users maximal heart rate at the warm-up period conclusion.

Immediately after the warm-up period the exercise should be more vigorous until target zone is reached. This segment should last 20 to 30 minutes. The pulse count is repeated at 5 minute intervals.

The cool down period is accomplished by easing up on the exercise over a 5 to 10 minute period before stopping. At the end of the cool down period, the pulse should be back to less than 50 percent of maximal obtainable heartbeat.

This program should be practiced no less than three times weekly. The problem, of course, is to encourage the user to be persistent in the program. All of the monitored parameters, along with the variable speed outdoor exercise display encourage the user to persist. This is enhanced by the fact that the user may refer to charts or his memory to know that he is within the target zone and to regulate his output, accordingly.

It is also possible for two or more persons to run on the same treadmill, double row or the like and a further display may be provided for any extra persons involved.

The heart of the system is the TV monitor and variable speed video cassette player, or the like. The other parameters are provided as an overall package arrangement to stimulate the user to maintain adherence to the program for physical fitness.

DESCRIPTION OF THE PRIOR ART

U.S. Pat. No. 3,929,335 is designed to motivate a patient in need of occupational therapy only for exercising his muscles. This is in contrast to the present invention which motivates a normal person to maintain his physical fitness. This patent is therapeutic following an injury or disease, whereas the subject system may be thought of as preventative medicine to maintain the subject in first class cardiovascular condition.

U.S. Pat. No. 3,712,613 is not directed to encouraging aerobic conditioning because it does not maintain the stimulus for 20 to 30 minute periods at 70 to 85 percent of maximum. In the patented device, the user is in an easy chair, and he would tend to do more resting than exercise. Additionally, no dynamic information relative to the performance is provided.

BRIEF DESCRIPTION OF THE DRAWINGS

The present invention will be better understood from the following detailed description thereof, when taken in light of the accompanying drawings wherein.

DESCRIPTION OF THE PREFERRED EMBODIMENTS

Figure 1:
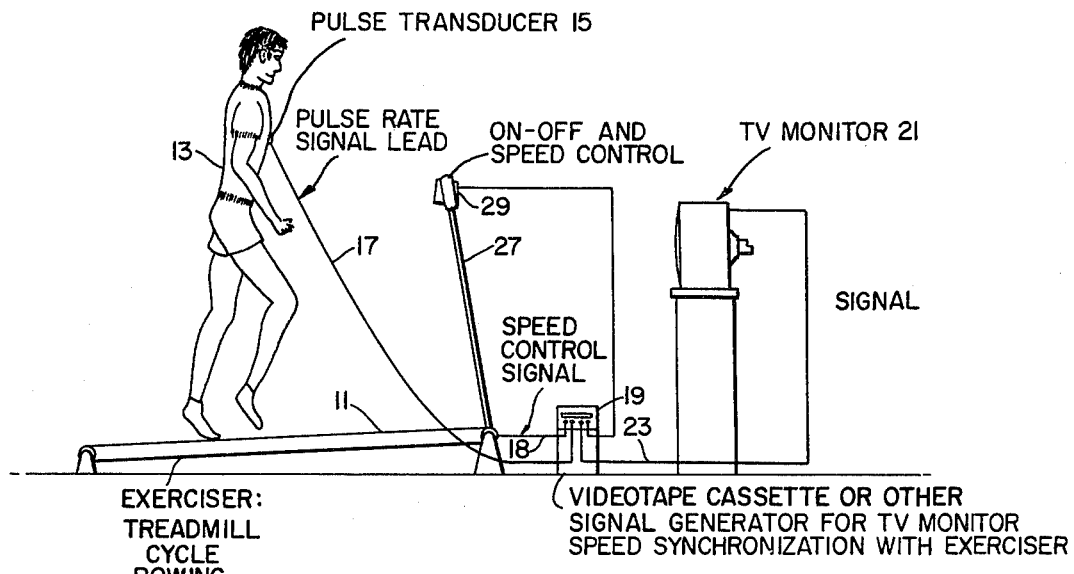
FIG. 1 is a representation of the user relative to the equipment.

In FIG. 1, a typical exerciser is shown as the treadmill 11, operated by the user 13. His pulse rate is picked up by pulse transducer 15, and transferred over signal lead 17 to TV monitor 21 via a circuit later to be described.

As treadmill 11 cycles, a magnetic or light beam pickoff generates a speed control signal, transferred over lead 18 to video tape cassette or other signal generator 19, for control of speed of the cassette, and, also for superposition on the video and further transfer over cable 23 to monitor 21.

A support 27 includes an on-off control 29, along with a speed control which, if used, may be manipulated by the user then by changing the relative speed of the video cassette patern with respect to the treadmill 13 to stay abreast of the target zone treadmill speed.

Figure 2:
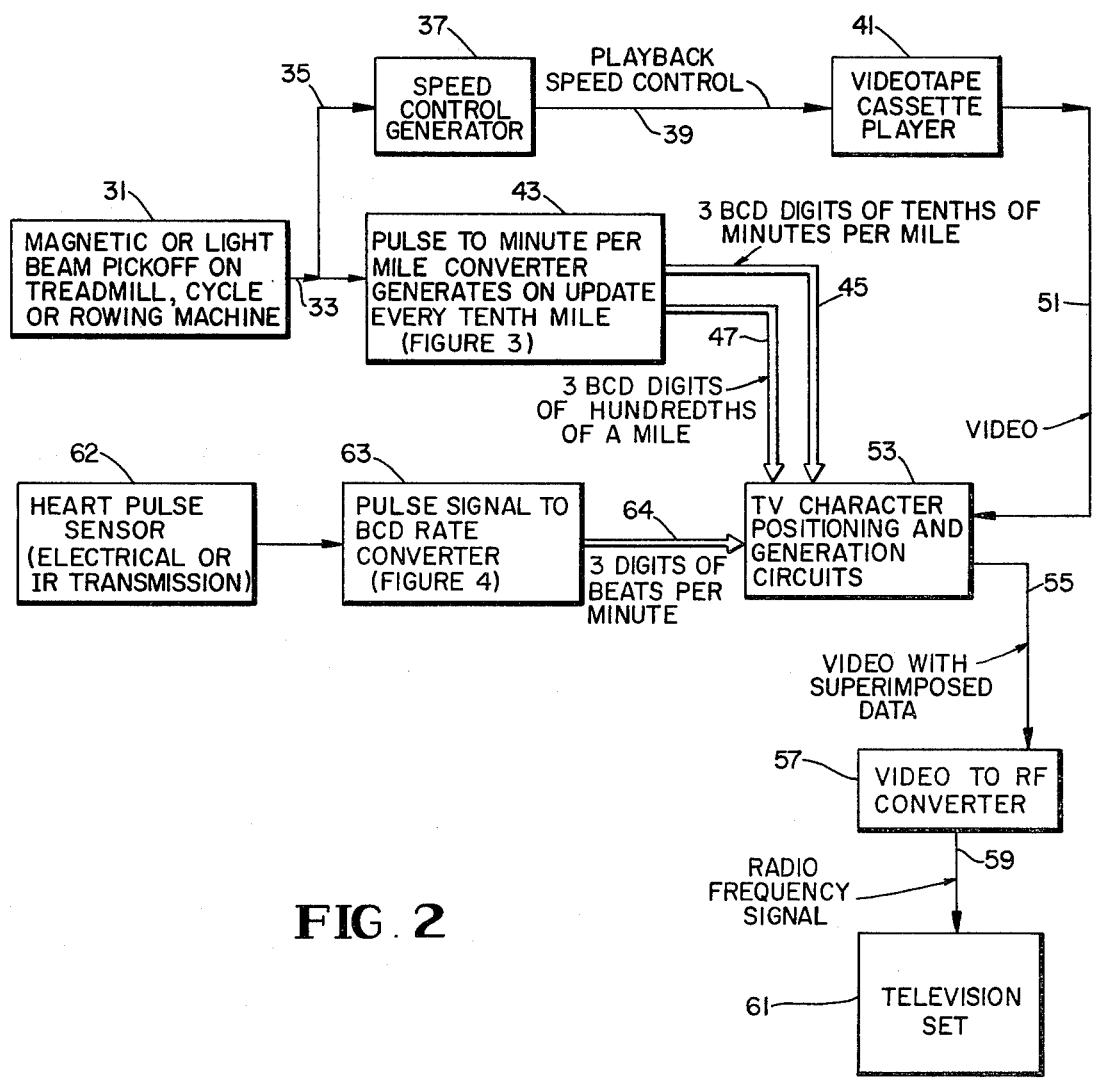
FIG. 2 is a block diagram of the preferred apparatus for carrying out the subject method.

In FIG. 2, a magnetic or light beam pickoff, associated with the treadmill, cycle, rowing machine or the like is illustrated at 31. It provides an electrical signal on lead 33 which signal pulses on every stroke of a lever or revolution of a wheel of the exerciser. This signal is provided, over lead 35, to a speed control generator 37, adapted to produce a playback speed control signal over lead 39 to video tape cassette player 41, or the like. Speed control generator 37 is conventional, and may produce a variable voltage or variable frequency signal to control the speed of video tape cassette player 41. Whether it is a variable frequency or variable voltage, depends on the particular type of video tape player being used. If it is a variable frequency signal, it can be generated by a phase lock loop frequency synthesizer tied to the exercise machine pulse output.

Also, the pulse train speed signal on lead 33 is directed to the converter timing circuitry 43. The circuitry 43 generates binary coded decimal signals on leads 45 and 47. The three digit BCD signal on lead 45 represents the users speed in minutes and tenths of a minute per equivalent mile. The signal on lead 47 represents the total number of miles to the hundreths of a mile.

These two signals, along with the video from video tape cassette player 41 (via lead 51) are applied to TV character positioning and generation circuits 53. The latter circuitry is conventional and merely superimposes the character data on the video for application over lead 55 to video to RF converter 57. The combination signal, consisting of the video with superimposed data, is converted to the radio-frequency signal applied over lead 59 to the television set, TV monitor, or the like 61.

Heart pulse sensor 62 develops a pulsing signal of heartbeat or blood pressure rate, converted to BCD at block 63 for 3 digit output on lead 64 to the TV character positioning and generation circuits 53. The 3 digits are beats per minute.

Figure 7:
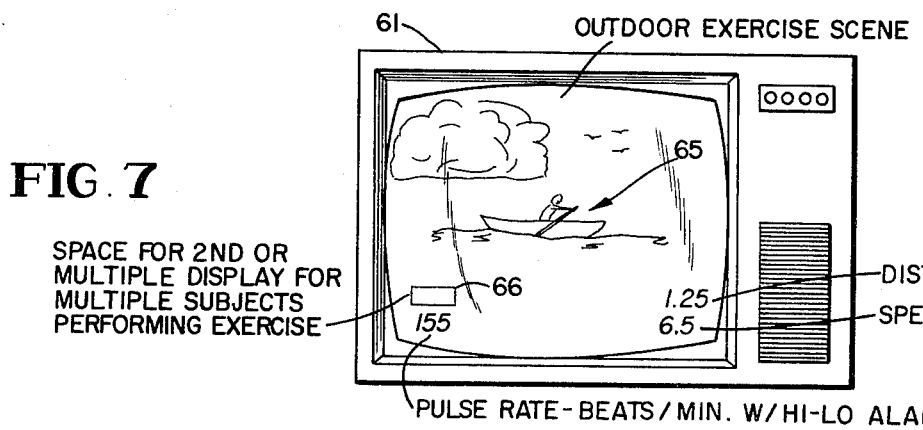
FIG. 7 is a pictorial view of the preferred monitor, illustrating a TV display.

In this manner, the pertinent data on TV monitor 61 (see FIG. 7) is available to the user. The video scene, by way of example, is the rowing scene 65, taking place in an outdoor background. The speed of the rower is increased or decreased in accordance with the speed of the user. The momentary speed is illustrated on the lower right hand corner of monitor 61 as the users speed of 6.5 minutes per mile. The distance thus far transversed, by the user, is shown directly above the speed as 1.25 miles.

Figure 5:
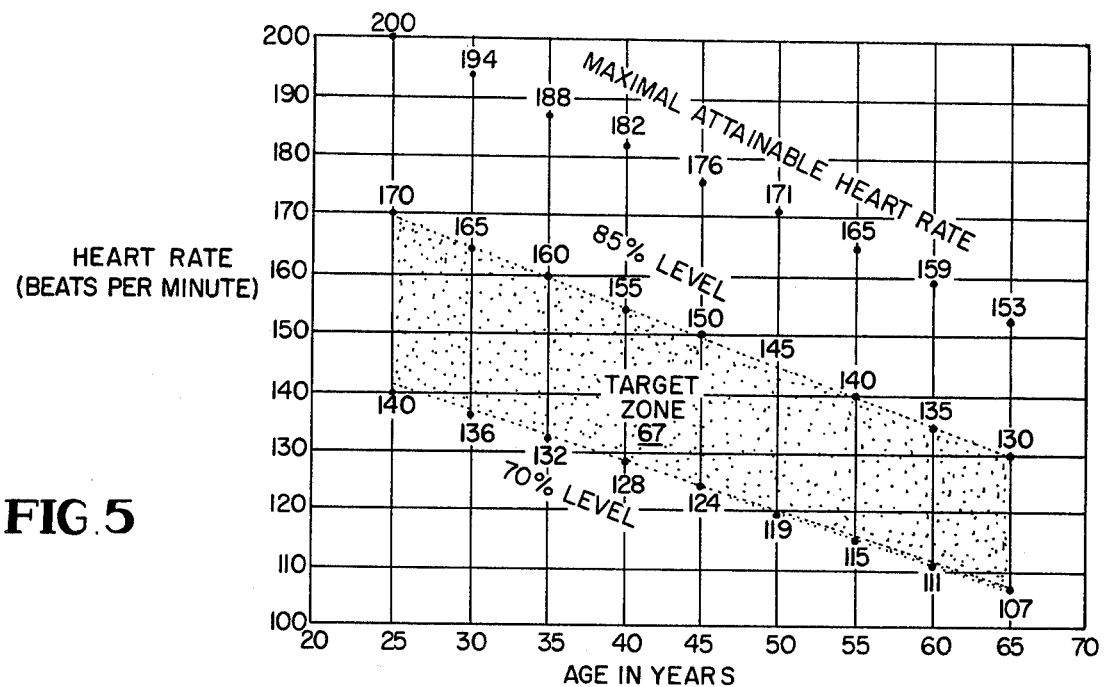
FIG. 5 is a chart showing the target zone defined by heart rate vs. age and years.

At the lower left of monitor 61, there appears the pulse rate, shown as 155, in hearbeats per minute, which rate may be high and low alarmed, according to the target zone region 67 of FIG. 5, as per age of user. Space 66, on monitor 61 is available for a comparison users pulse rate, the other parameters being the same as the users.

Figure 3:
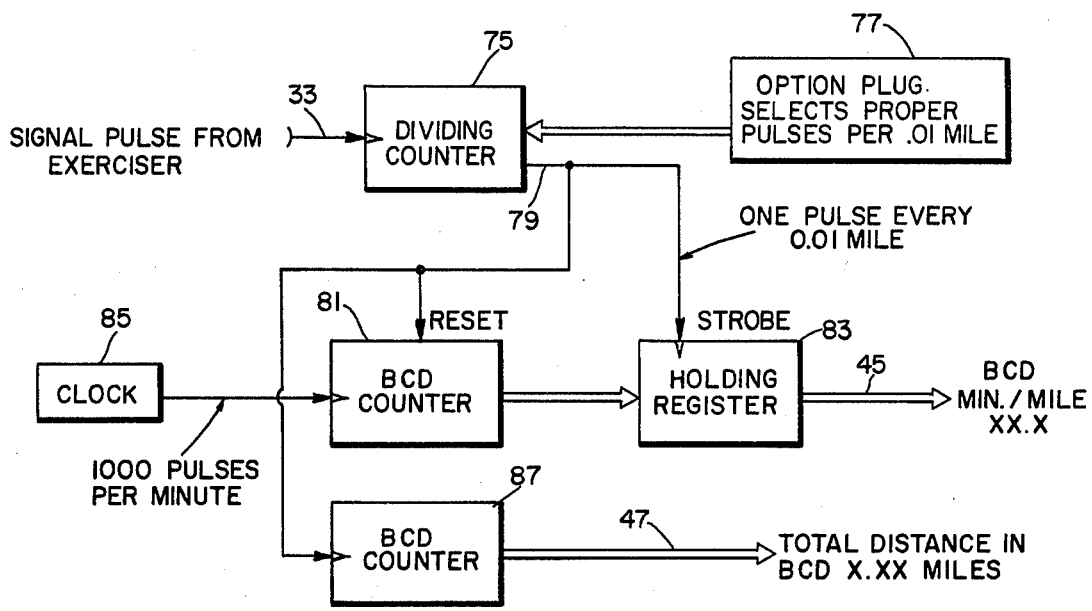
FIG. 3 is a detailed block diagram of a portion of the diagram of FIG. 2.

Turning now to FIG. 3, further detail is illustrated with respect to counter-timer 43 of FIG. 2. The input pulse train on lead 33 is applied to dividing counter 75. Counter 75 may be of the divided-by-N integrated circuit type with N being selected by a jumpered plug or switch 77 so as to match the exercise machine 11. For example, N may range from 10 (for a rowing machine) to 100 (for a treadmill). N is selected as being the number of pulses on input lead 33 per equivalent hundredth of a mile.

The output 79, from dividing counter 75 is used to gate the time pulse counting circuit, shown as the BCD counter 81, and the holding register 83, at each hundredth of a mile.

Clock 85 provides a constant output of 1000 pulses per minute to BCD counter 81, such that the speed reciprocal in minutes per mile appears as the BCD output 45 to the tenth order.

The dividing counter 75, also energizes the distance BCD counter 87 to provide the distance on lead 47 in BCD to the hundredths order of equivalent miles.

Figure 4:
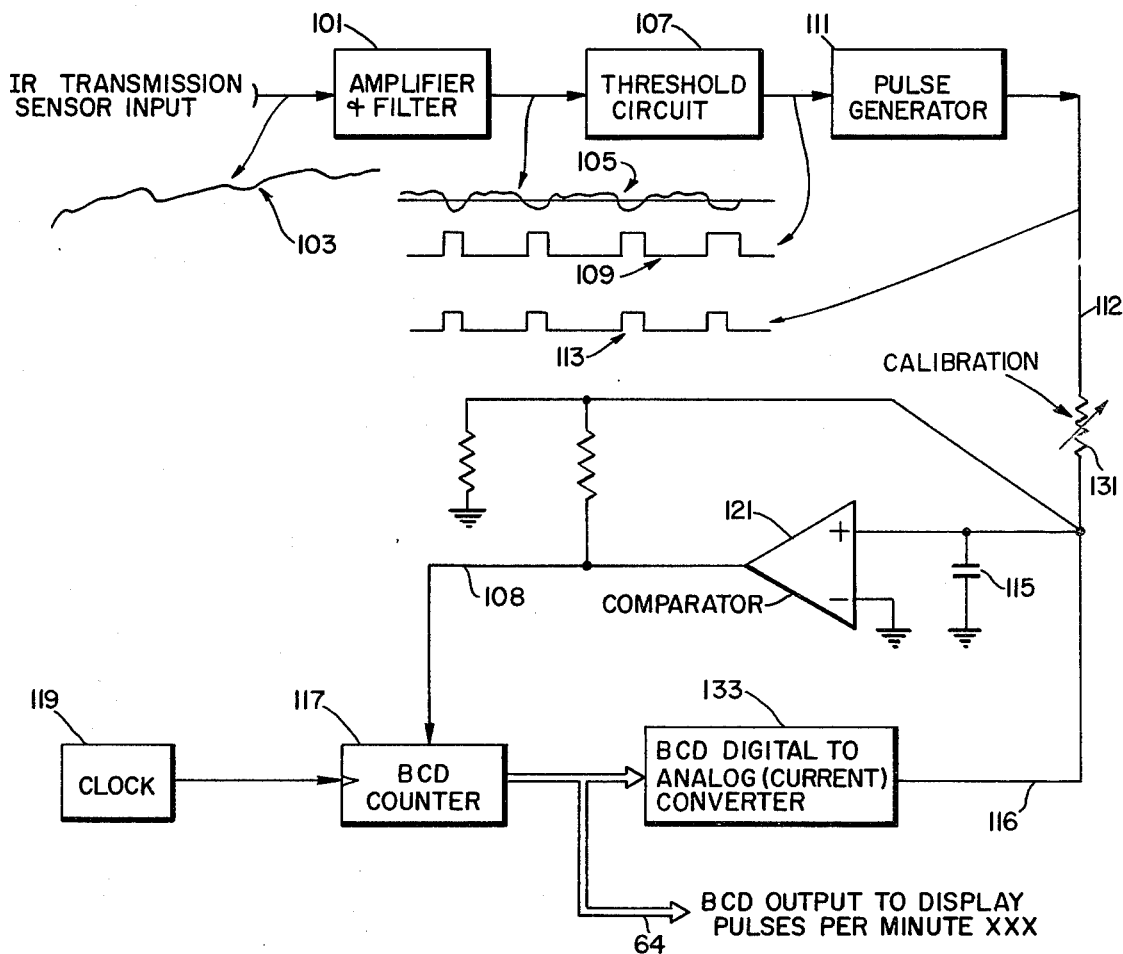
FIG. 4 is a further block drawing with waveforms of a further portion of the apparatus of FIG. 2.

In FIG. 4, one method of implementing the pulse-rate to BCD converter 63 (FIG. 2) circuitry is detailed. The input electrical signal from the heart pulse sensor 62 from either electrodes on the users body or an infra red transmission transducer (on an ear lobe or finger) is amplified and band-pass filter in the amplifier filter unit 101 to change the heart pulsing signal from that pictured at 103 (FIG. 4) to the wave form 105. Signal 105 is applied to threshold detector 107, which generates the square pulses, shown as the wave train 109. Square pulse train 109 is fed to pulse generator 111 to produce a constant amplitude, constant width pulse train 113.

These uniform pulses 113 charge capacitor 115 at the same time that it is being discharged by a current proportional to the count at lead 64 (i.e. BCD counter 117 output) to display pulses per minute (to three figures). The discharging current flows through lead 116 relative to the charging current on lead 112. The output from the comparator 121 on lead 108 will cause the count at a counter to increment if current on lead 116 is less than current on 112 and decrement if visa versa.

The frequency of the clock 119 to the counter 117 should be about half the nominal heartbeat rate (pulse or minus 50%). The BCD output at lead 64 from the up-down counter 117 will thus be proportional to the heartbeat rate and may be calibrated by the resistor 131. Digital to analog converter 133 is a current converter for the BCD output (count) of counter 117 to analog current at lead 116 for algebraic combination with the current on lead 112 in controlling the charge and discharge of capacitor 115.

TV character positioning and generation circuits 53 of FIG. 1 may be large scale integrated circuits, such as Texas Instrument Model SN76460. Alternatively, but less preferable, are integrated circuit counters coupled with an oscillator and ROM for performing similar functions. These circuits are simply used to determine the TV spots vertical position (by counting horizontal lines) and horizontal position (by counting the oscillator's output). Thus at the proper counts, the output from the ROM would be used to superimpose the body of a number onto the video from the video tape player, creating the BCD numbers on screen 61. These techniques are known from TV game techniques, for moving the ball in games, such as tennis and ping pong, and the superimposition of data on video is seen every day on TV screens.

The video-to-RF converter 57, converts the video signal into a radio frequency signal for display on an ordinary TV set, such as 61. These are also off-the-shelf components.

Figure 6:
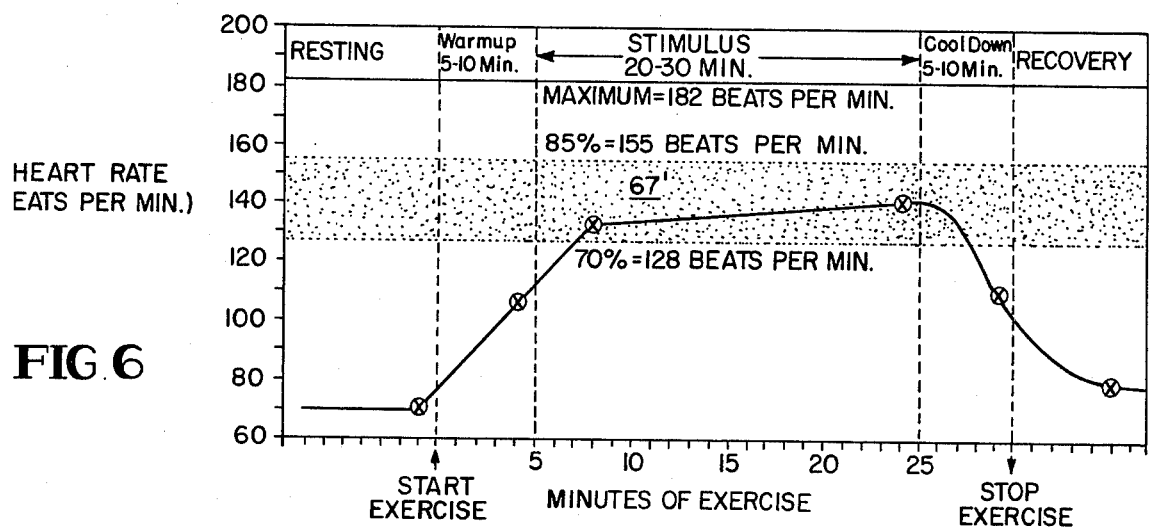
FIG. 6 is a further chart, based on target zone, but delineating the preferred range of minutes of exercise for a typical program per day or every other day.

The charts of FIGS. 5 and 6 have been generally explained heretofore. For example, in FIG. 5, the target zone 67 for a 40 year old person is between 128 and 155 heartbeats per minute. This is 70 to 85 percent of the maximal obtainable heart rate of 182 for such a 40 year old user.

In FIG. 6 the chart explains the warm-up heartbeat in terms of minutes of exercise. It should be noted that the target zone 67' should not be obtained until after the warm-up period, as explained.

What is claimed is:

1. A user controlled exercise monitoring system for user selection of an exercise program within a programmed heartbeat range comprising the combination:
    (a) a movable variable speed exerciser powered exercise mechanism movable at a variably controlled speed selectable by the physical activity of an exercising user in an aerobic type exercise program,
    (b) a variable speed visible display system providing a scene observable by the user while powering said mechanism to produce a movable pattern related to the aerobic exercise and movable at a variable speed controlled by said exercise mechanism,
    (c) manually actuated speed control means accessible to the exerciser for changing the speed of the movable pattern while powering said mechanism connecting the mechanism to the display for variably controlling at the command of the user the relative speed of said movable pattern with respect to the exercise mechanism, (d) and heartbeat detection means including a sensor for operably coupling to the exercising user and conversion equipment for displaying continuously the heartbeat pulse rate of the exerciser user on said visible display as an auxiliary display visible along with said scene with an alarm indication when the pulse rate departs from a specified target zone, thereby to permit the user at his option by control of his exercise speed to maintain a vigorous exercise program over a sustained time period while observing whether the pulse rate is within said target zone.

2. The system of claim 1 wherein said scene is recorded on a variable speed video tape cassette capable of displaying the movable pattern at said variably controlled speed whereby the speed of operation of said video tape cassette player therefor is controllable by said speed control means under control of the exerciser.

* * * * *